(12) United States Patent
Hutchinson

(10) Patent No.: US 7,056,292 B2
(45) Date of Patent: Jun. 6, 2006

(54) SYSTEM AND METHOD OF MONITORING SYSTOLIC PRESSURE VARIATION

(75) Inventor: George Martin Hutchinson, Milwaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 217 days.

(21) Appl. No.: 10/837,165

(22) Filed: Apr. 30, 2004

(65) Prior Publication Data

US 2005/0245830 A1 Nov. 3, 2005

(51) Int. Cl.
*A61B 5/02* (2006.01)

(52) U.S. Cl. .................. 600/485; 600/301; 600/481; 600/529

(58) Field of Classification Search ............ None
See application file for complete search history.

(56) References Cited

U.S. PATENT DOCUMENTS

| 5,769,082 | A | 6/1998 | Perel | |
|---|---|---|---|---|
| 6,585,658 | B1 * | 7/2003 | Redaelli et al. | 600/484 |
| 2003/0167010 | A1 | 9/2003 | Pinsky | |

OTHER PUBLICATIONS

"Systolic blood pressure at end-expiration measured by the automated systolic pressure variation monitor is equivalent to systolic blood pressure during apnea" by Schwid et al. Journal of Clinical Monitoring and Computing 16:115-200, 2000.*

Richard E. Klabunde, Ph.D., Cardiovascular Physiology Concepts, Arterial Blood Pressure; http://www.cvphysiology.com/Blood%20Pressure/BP002.htm.

Richard E. Klabunde, Ph.D., Cardiovascular Physiology Concepts, Mean Arterial Pressure; http://www.cvphysiology.com/Blood%20Pressure/BP006.htm.

Richard E. Klabunde, Ph.D., Cardiovascular Physiology Concepts, Arterial Pulse Pressure; http://www.cvphysiology.com/Blood%20Pressure/BP003.htm.

Scott R. Gunn, et al., Implications of arterial pressure variation in patients in the intensive care unit; Current Opinion in Critical Care, 2001, pp. 212-217.

Frederic Michard, M.D., et al.; Predicting Fluid Responsiveness in ICU Patients; Chest, Critical Care Reviews, Jun. 2002, pp. 2000-2008.

(Continued)

*Primary Examiner*—Robert L. Nasser
*Assistant Examiner*—Patricia Mallari

(57) ABSTRACT

System and method of monitoring a patient including acquiring a respiration waveform and an arterial pressure waveform and determining a window on the respiration waveform that represents end expiration and approximates an apnea condition. The method can include calculating a systolic pressure variation value, a delta up value, and a delta down value based on a portion of the arterial pressure waveform corresponding to the window on the respiration waveform. In some embodiments, the respiration waveform can be acquired without manual interruption of mechanical ventilation and the values can be calculated substantially continuously.

17 Claims, 4 Drawing Sheets

OTHER PUBLICATIONS

Ajd Parry-Jones, et al., Arterial pressure and stroke volume variability as measurements for cardiovascular optimisation; International Journal of Intensive Care, Summer 2003, pp. 1-5.

Daniel M. Joyce, Ventilator Management; http://www.emedicine.com/emerg/topic788.htm; pp. 1-11.

Physiologic Monitoring in the Trauma Patient What's Old, What's New?, http://www.trauma.org/anaesthesia/monitoring.html; pp. 1-12.

Frederic Michard, et al.; Using heart-lung interactions to assess fluid responsiveness during mechanical ventilation; Critical Care 2000, vol. 4, No. 5, Sep. 1, 2000, pp. 282-289; http://ccforum.com/content/4/5/282.

Richard E. Klabunde, Ph.D., Cardiovascular Physiology Concepts, Pathophysiology of Heart Failure; pp. 1-3; http://www.cvphysiology.com/Heart%20Failure/HF003.htm.

Andre Y. Denault, et al., Determinants of Aoritic Pressure Variation During Positive-Pressure Ventilation in Man; Chest, Clinical Investigations in Critical Care; Jul. 1999, pp. 176-186.

Frederic Michard, et al., Relation between Respiratory Changes in Arterial Pulse Pressure and Fluid Responsiveness in Septic Patients with Acute Circulatory Failure; Am J Respir Crit Care Med, vol. 162, 2000; pp. 134-138.

Elliott Bennett-Guerrero, et al., Comparison of Arterial Systolic Pressure Variation with Other Clinical Parameters to Predict the Response to Fluid Challenges during Cardiac Surgery, The Mountsinai Journal of Medicine, Jan./Mar. 2002, pp. 96-100.

Thomas Buckingham, Use of Arterial Pressure and Stroke Volume Variation Predicts Response to Fluids in Mechanically Ventilated Patients; http://www.docguide.com/news/content.nsf/NewsPrint/8525697700573E1885256CEF007; pp. 1-2.

* cited by examiner

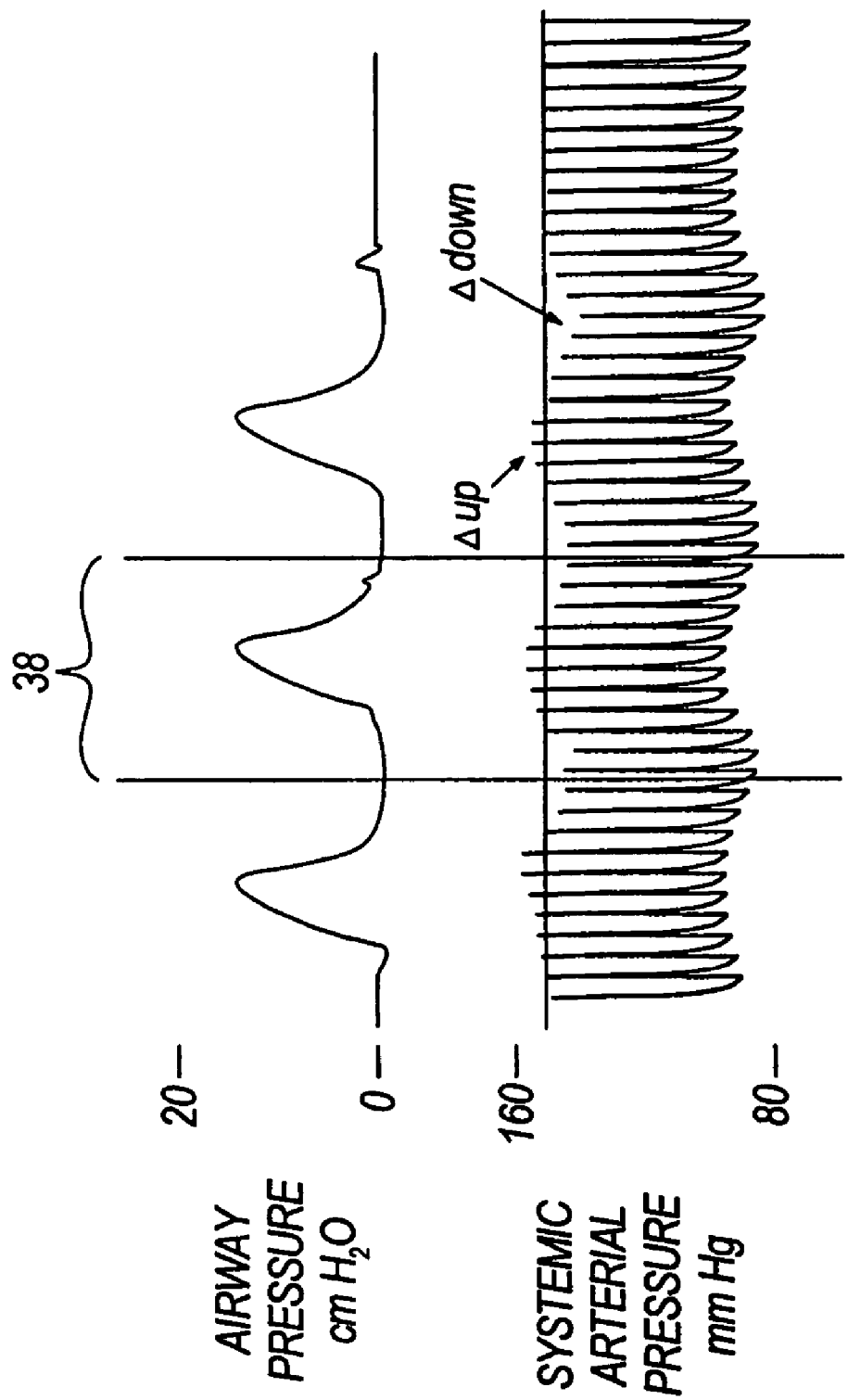

SYSTEM AND METHOD OF MONITORING SYSTOLIC PRESSURE VARIATION

BACKGROUND

The cardiovascular status of a patient that is being mechanically ventilated is important to medical care practitioners in order to provide adequate monitoring and treatment of the patient. Several techniques have been used to assess cardiac function, such as measurement of central venous pressure by a catheter that is introduced through a vein into the right atrium and measurement of the pulmonary capillary wedge pressure by the insertion of a Swan-Ganz catheter (a balloon-tipped pulmonary artery catheter).

Calculations made from systolic blood pressure waveforms are also used to assess cardiac function in mechanically ventilated patients. However, acquiring these calculations requires manipulation of the ventilator, i.e., turning the ventilator off for a period of time to generate an apneic episode. This method prevents the continuous measurement of the systolic blood pressure.

BRIEF DESCRIPTION OF THE INVENTION

One embodiment of the invention includes a method of monitoring a patient. The method comprises acquiring a respiration waveform and a systolic pressure waveform from the patient, determining a window on the respiration waveform that represents end expiration and approximates an apnea condition, and calculating at least one of a systolic pressure variation value, a delta up value, and a delta down value based on at least a portion of the systolic pressure waveform corresponding to the window on the respiration waveform.

In another embodiment, the invention includes a method of monitoring a patient connected to a ventilator. The method comprises acquiring a respiration waveform from the patient without manually interrupting the ventilator, determining a window on the respiration waveform that represents end expiration and approximates an apnea condition, acquiring a systolic pressure waveform from the patient, the systolic pressure waveform including systolic pressure values that correspond to the window of the respiration waveform, averaging the systolic pressure values to determine a reference systolic pressure value, and calculating at least one of a systolic pressure variation value, a delta up value, and a delta down value based on the reference systolic pressure value.

BRIEF DESCRIPTION OF THE DRAWINGS

FIG. 4 is a graphical illustration of a systolic pressure waveform and a respiration waveform.

DETAILED DESCRIPTION

Figure 1:
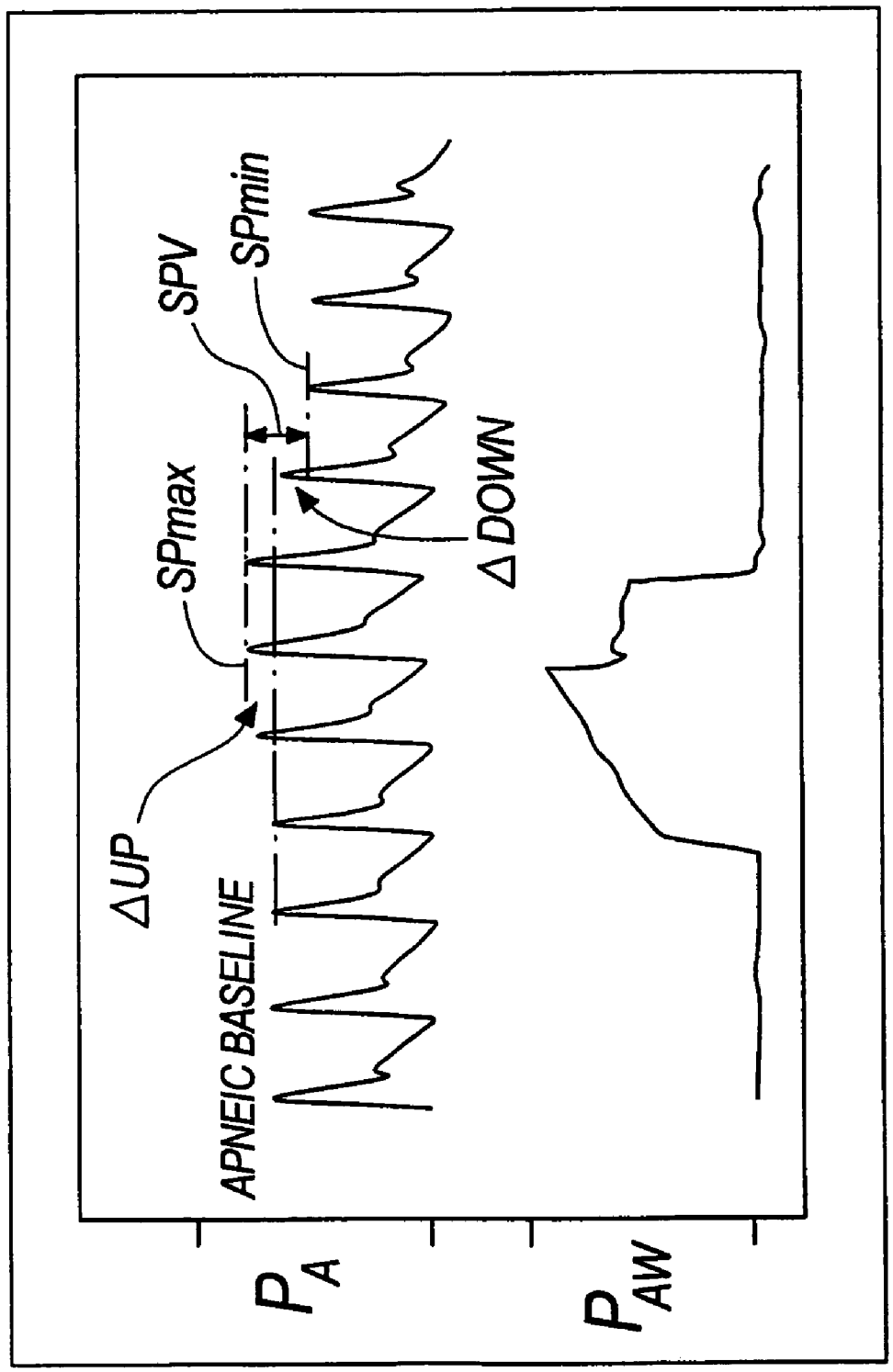
FIG. 1 is a graphical illustration of various components of a systolic pressure waveform and a respiration waveform.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Measurements used in assessing cardiovascular status while a patient is mechanically ventilated can include systolic pressure variation, delta up, and delta down. FIG. 1 illustrates an arterial pressure waveform $P_A$ and a respiration waveform $P_{AW}$. The arterial pressure waveform of FIG. 1 identifies the systolic pressure variation SPV, delta up $\Delta$Up, delta down $\Delta$Down, the maximum systolic pressure $SP_{max}$, and the minimum systolic pressure $SP_{min}$. Systolic pressure variation is generally defined as the difference between the maximum and minimum values of systolic blood pressure following a single positive pressure breath. Systolic blood pressure is generally defined as the maximum pressure exerted by contraction of the heart. Systolic blood pressure is generally measured at the peak of ventricular contraction (e.g., systole). The delta up value is generally defined as the difference between the maximum value of the systolic pressure and a reference systolic pressure. The reference systolic pressure is the average systolic blood pressure during a short period of apnea. The delta up value can represent the inspiratory increase in systolic pressure, which results from an increase in left ventricular stroke volume. The delta down value is generally defined as the difference between the reference systolic pressure and the minimum value of the systolic pressure. The delta down value can represent the expiratory decrease in left ventricular stroke volume that occurs due to the decrease in the amount of blood entering the right heart (i.e., venous return).

Systolic pressure variation can reflect the fluctuation of the systolic blood pressure caused by mechanical ventilation. In a positive pressure ventilation setting on the mechanical ventilator, positive pressure (relative to atmosphere) can be applied to the patient's airway opening. The ventilator can deliver gas to the patient through a set of flexible tubes (e.g., endotracheal tubes or tracheotomy tubes) that can be connected to the patient's throat or a mask that can cover the patient's mouth and/or nose.

With a positive pressure ventilator, inspiration causes an increase in intrathoracic pressure which propels blood out of the vasculature of the lungs and into the left atrium and left ventricle of the heart. This increase in intrathoracic pressure can cause an increase in left ventricular preload, stroke volume, and systolic blood pressure. In addition, this increase in intrathoracic pressure can result in reduced venous return to the right atrium, which can cause a decrease in any one of left ventricular filling, preload, stroke volume, and systolic blood pressure. Delta up can be determined by using the systolic blood pressure at the end of expiration, and delta down can be determined by using the systolic blood pressure during inspiration.

The magnitude of the systolic pressure variation measurement can be affected by a number of factors, such as lung and chest wall compliance, tidal volume, cardiac function, and volume status. If the ventilation parameters remain constant, changes in the intravascular volume status of the patient can influence the magnitude of the systolic pressure variation. As a result, systolic pressure variation, delta up, and delta down values can be used to determine the patient's fluid status.

Figure 2:
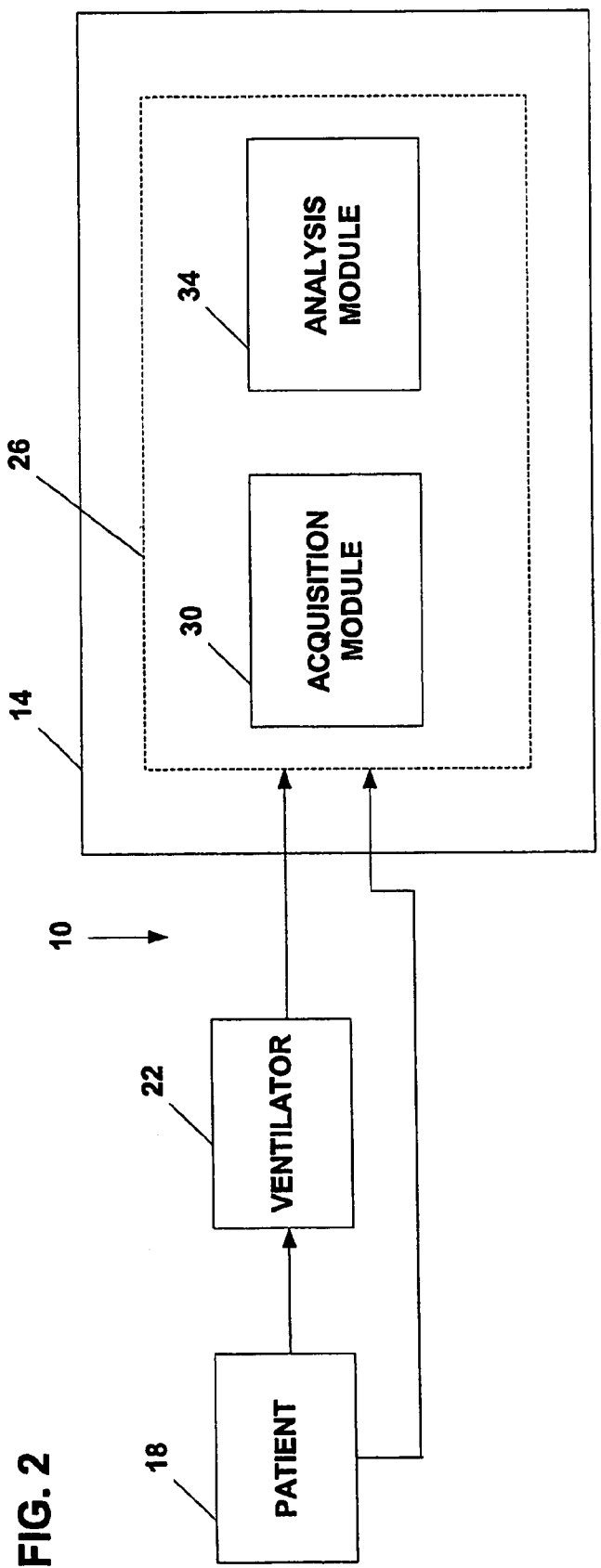
FIG. 2 is a schematic illustration of a patient data analysis system according to one embodiment of the invention.

According to one embodiment of the invention, FIG. 2 illustrates a system 10 that can interconnect with various pieces of medical equipment and can monitor a patient's physiological status. The system 10 can include a patient data analysis system 14 that is connected to a patient 18 and a piece of medical equipment, such as a ventilator 22. The patient data analysis system 14 can include a software program(s) 26 that can be manipulated by a computer terminal(s) (not shown) and/or other medical equipment to acquire, enter, review, analyze, and/or save information.

The software program(s) 26 can include an acquisition module 30, which can acquire and/or receive data from the patient 18 and/or the ventilator 22. The data can include measurements; waveforms; raw data; unanalyzed data; analyzed data; images; charts; graphs; identified abnormalities; normal and abnormal ranges; and patient identifiers (e.g., name, age, sex, weight, race). The software program(s) 26 can also include an analysis module 34, which can analyze the acquired data for the patient 18. The acquisition module 30 and/or the analysis module 34 can include a separate software program (not shown) and/or additional software programs. In some embodiments of the invention, the patient data analysis system 14 can include a server (not shown) and/or a database (not shown) for storing patient data information. The server can include an operating system for running various software programs and/or a communications application. The software programs can be manipulated by computer terminals (not shown) and/or medical equipment to acquire, enter, review, and/or save information.

Other embodiments of the invention can include fewer or more pieces of medical equipment or components than those shown in FIG. 2. The system 10 can include any suitable number and combination of pieces of medical equipment, modules, and/or components that can communicate with one another and/or over a network (not shown).

Figure 3:
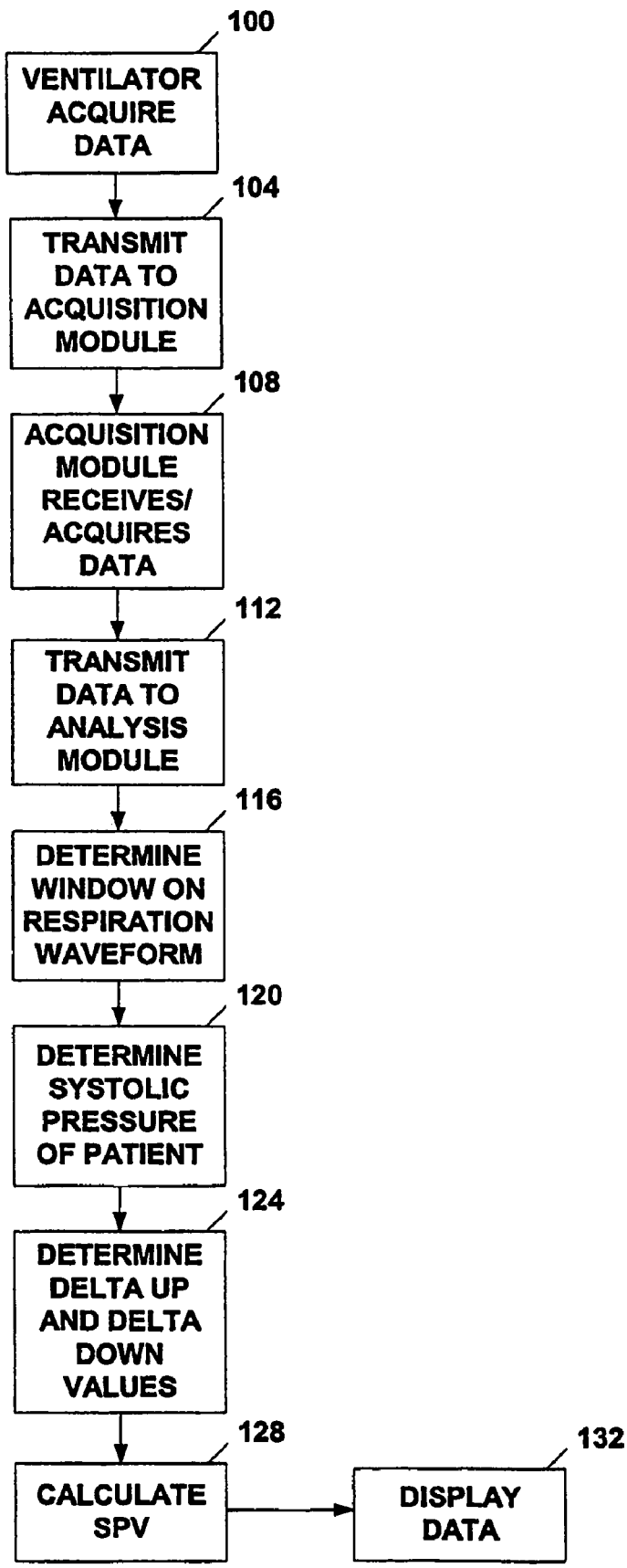
FIG. 3 is a flow chart illustrating the operation of the patient data analysis system of FIG. 2 according to one embodiment of the method of the invention.

FIG. 3 is a flow chart illustrating one embodiment of the method of the invention. The ventilator 22 can be connected to the patient 18 via tubing (e.g., endotracheal tubes or tracheotomy tubes) or a mask. The ventilator 22 can acquire (at 100) data from the patient, such as a respiration waveform $P_{AW}$ (as shown in FIG. 4), respiration data (e.g., $CO_2$, tidal volume, airway flow, airway volume, etc.), and an arterial pressure waveform $P_A$ (as shown in FIG. 4). The ventilator 22 can transmit (at 104) the data to the acquisition module 30. The acquisition module 30 of the patient data analysis system 14 can acquire (at 108) other data from the patient, such as waveforms and quantitative data related to the patient's ECG, blood pressure, pulse oximetry, heartbeat, etc.

The acquisition module 30 can transmit (at 112) the data to the analysis module 34 where the data from the ventilator 22 and the patient 18 can be combined and synchronized. In general, a series of respiratory cycles can be examined using both a respiratory waveform (e.g., airway $CO_2$, airway volume, airway flow, and/or airway pressure) and an arterial pressure waveform to determine the systolic pressure at end-expiration. This method can be used to approximate the conditions found during a period of apnea. The approximation generally becomes more accurate at larger inspiration-to-expiration ratios. More specifically, the analysis module 34 can determine (at 116) a window 38 (see FIG. 4) on the respiration waveform that represents end expiration, which provides an approximation of apnea. The analysis module 34 can determine (at 120) the systolic pressure variation of the patient 18 at end expiration based on the systolic pressure waveform and corresponding systolic pressure values (as shown in FIG. 4) within the window 38. The systolic pressure values that fall within the window 38 can be averaged together or otherwise entered into an algorithm to determine a reference systolic pressure value for the window 38.

As a result, with the measurement of systolic pressure during an approximation of apnea, the analysis module 34 can calculate the systolic pressure variation, the delta up value, and the delta down value without manual interaction with the ventilator. The analysis module 34 can determine (at 124) the delta up value and the delta down value within the window 38 by calculating the magnitude difference between the highest systolic pressure value and the reference value (for the delta up value) and the magnitude difference between the lowest systolic pressure value and the reference value (for the delta down value). After determining the systolic pressure, delta up, and delta down values, the analysis module can calculate (at 128) the systolic pressure variation value. In general, the analysis module 34 can use an averaged end-expiratory time from a ventilatory waveform to determine the systolic pressure that would have been present during an apnea period in order to calculate values for systolic pressure variation, delta up, and delta down.

The analysis module 34 can transmit the data for display (at 132) at the patient data analysis system 14. The data also can be printed on reports and/or a strip chart from a printer (not shown) either local or remote from the patient data analysis system 14. Based on the systolic pressure variation value, the delta up value, and the delta down value, medical care personnel can determine if the patient 18 needs fluids. The medical personnel also can monitor how the patient 18 responds to fluids that have been delivered to the patient 18 by watching the systolic pressure values, delta up values, and delta down values over time.

Various features and advantages of the invention are set forth in the following claims.

What is claimed is:

1. A method of monitoring a patient, the method comprising:
acquiring a respiration waveform and an arterial pressure waveform from the patient;
determining a window on the respiration waveform that represents end expiration and approximates an apnea condition; and calculating at least one of a systolic pressure variation value, a delta up value, and a delta down value based on at least a portion of the arterial pressure waveform corresponding to the window on the respiration waveform.

2. The method of claim 1 and further comprising mechanically ventilating the patient using a ventilator and determining a window on the respiration waveform that approximates an apnea condition without manually interacting with the ventilator.

3. The method of claim 1 and further comprising calculating at least one of the delta up value by determining the difference between a maximum value of systolic pressure and a reference systolic pressure and the delta down value by determining the difference between a reference systolic pressure and a-minimum value of systolic pressure.

4. The method of claim 3 and further comprising averaging at least two systolic pressure values to calculate the reference systolic pressure.

5. The method of claim 4 and further comprising averaging at least two systolic pressure values within the window to calculate the reference systolic pressure.

6. The method of claim 1 and further comprising determining an intravascular volume status of the patient based on at least one of the systolic pressure variation value, the delta up value, and the delta down value.

7. The method of claim 1 and further comprising acquiring and analyzing a series of respiratory cycles to determine a window and to calculate at least one of a systolic pressure variation value, a delta up value, and a delta down value.

8. The method of claim 1 and further comprising acquiring at least one respiration waveform representing at least one of airway carbon dioxide, airway pressure, airway volume, and airway flow.

9. The method of claim 1 and further comprising continuously acquiring a respiration waveform and a systolic pressure waveform without manual interruption of mechanical ventilation.

10. The method of claim 9 and further comprising continuously calculating at least one of the systolic pressure variation value, the delta up value, and the delta down value.

11. The method of claim 1 and further comprising determining a fluid status of the patient based on at least one of the systolic pressure variation value, the delta up value, and the delta down value.

12. A computer program embodied by a computer readable medium capable of being executed by a computer, the computer program for use in a patient monitoring system, the computer program comprising:

an acquisition module that communicates with a ventilator to acquire a respiration waveform and an arterial pressure waveform from a patient; and an analysis module that determines a window on the respiration waveform that represents end expiration and that approximates an apnea condition, the analysis module calculating at least one of a systolic pressure variation value, a delta up value, and a delta down value based on at least a portion of the arterial pressure waveform corresponding to the window on the respiration waveform.

13. A method of monitoring a patient connected to a ventilator, the method comprising:

acquiring a respiration waveform from the patient without manually interrupting the ventilator;

determining a window on the respiration waveform that represents end expiration and approximates an apnea condition;

acquiring an arterial pressure waveform from the patient, the arterial pressure waveform including systolic pressure values that correspond to the window of the respiration waveform;

averaging the systolic pressure values to determine a reference systolic pressure value; and calculating at least one of a systolic pressure variation value, a delta up value, and a delta down value based on the reference systolic pressure value.

14. The method of claim 13 and further comprising determining an intravascular volume status of-the patient based on at least one of the systolic pressure variation value, the delta up value, and the delta down value.

15. The method of claim 13 and further comprising calculating at least one of the delta up value by determining the difference between a maximum value of systolic pressure and the reference systolic pressure and the delta down value by determining the difference between the reference systolic pressure and a minimum value of systolic pressure.

16. The method of claim 13 and further comprising acquiring and analyzing a series of respiratory cycles to determine the window and to calculate at least one of a systolic pressure variation value, a delta up value, and a delta down value.

17. The method of claim 13 and further comprising acquiring at least one respiration waveform representing at least one of airway carbon dioxide and airway pressure.

* * * * *